(12) United States Patent
Chen

(10) Patent No.: US 6,452,123 B1
(45) Date of Patent: Sep. 17, 2002

(54) SURGICAL FOOT PEDAL CONTROL INCLUDING RIBBON SWITCH ARRANGEMENT

(75) Inventor: Jerry S. J. Chen, Orange, CA (US)

(73) Assignee: Advanced Medical Optics, Santa Ana, CA (US)

( * ) Notice: Subject to any disclaimer, the term of this patent is extended or adjusted under 35 U.S.C. 154(b) by 14 days.

(21) Appl. No.: 09/607,431

(22) Filed: Jun. 27, 2000

(51) Int. Cl.7 .................................................. H01H 3/14
(52) U.S. Cl. ........................... 200/86.5; 606/32; 606/41
(58) Field of Search ............................... 200/86.5, 86 R, 200/61, 89; 74/512, 1; 307/119; 604/19, 27; 606/32, 41; 128/760

(56) References Cited

U.S. PATENT DOCUMENTS

| 4,293,752 A | * | 10/1981 | Koenig | 200/86 R |
| 5,091,656 A | | 2/1992 | Gahn | 307/119 |
| 5,554,894 A | | 9/1996 | Sepielli | 307/119 |
| 5,700,240 A | * | 12/1997 | Barwick, Jr. et al. | 604/22 |
| 5,983,749 A | * | 11/1999 | Holtorf | 74/512 X |
| 6,051,797 A | * | 4/2000 | Meinel | 200/86.5 |
| 6,150,623 A | * | 11/2000 | Chen | 200/86.5 |

* cited by examiner

Primary Examiner—J. R. Scott
(74) Attorney, Agent, or Firm—Walter A. Hackler; Peter Jon Gluck

(57) ABSTRACT

Apparatus for controlling a handpiece during surgery generally includes a foot pedal pivotally mounted to a base for enabling depression thereof in order to provide control signals for handpiece operation. At least one support surfaces provided adjacent the foot pedal on the base at a position enabling access thereto by a user's foot. A ribbon switch as disposed on the support surface and has a length sufficient enable actuation thereof by a user's foot without visual observation thereof by the user. The ribbon switch is actuable by depression thereof at any point along the length of the ribbon switch in order to provide additional control signals to the handpiece.

20 Claims, 1 Drawing Sheet

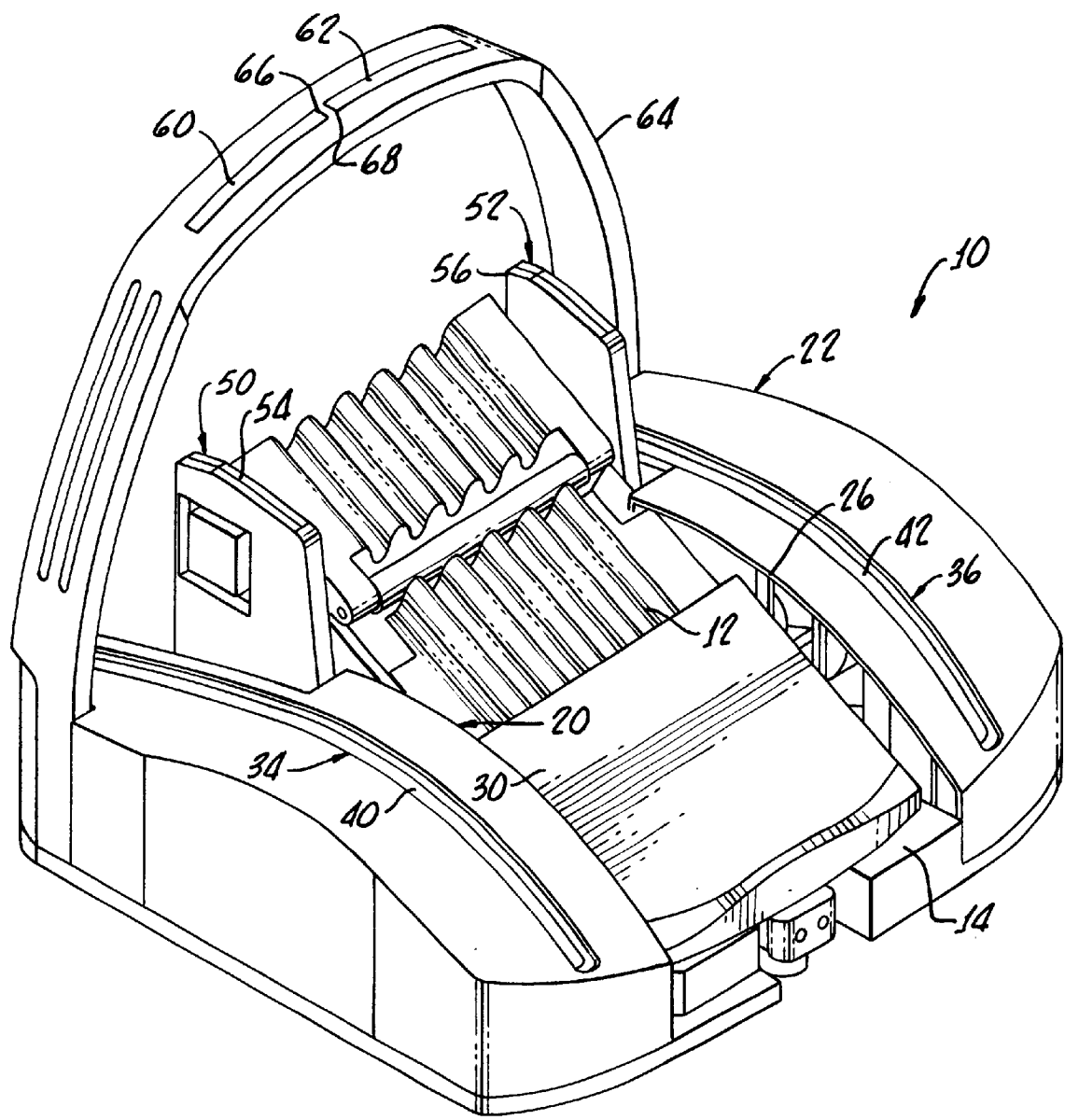

SURGICAL FOOT PEDAL CONTROL INCLUDING RIBBON SWITCH ARRANGEMENT

The present invention generally relates to apparatus for controlling various apparatus and is more particularly directed to a foot operated control for ophthalmic surgical apparatus such as, for example, for controlling the operation of handpieces during ophthalmic surgery. Still more particularly, the present invention is directed to apparatus for the control of irrigation, aspiration in connection with phacoemulsification of natural lenses.

Ophthalmic surgical apparatus such as phacoemulsification apparatus, hereinabove noted, typically includes operating controls for regulating parameters, or functions, of the apparatus. The apparatus generally includes a handpiece for ultrasonic emulsifying a natural lens while irrigating the eye and aspirating particles of emulsified lens.

Various modalities of operation may be utilized in phacoemulsification apparatus which pertain to controlling various phases of the phacoemulsification procedure.

Typical apparatus includes a control cabinet, power supply, vacuum pump, as well as associated electronic hardware for operating multi-function handpiece in order to sonically emulsify eye tissue, irrigate the eye with saline solution, and aspirate the emulsified lens from the eye.

The control system typically utilizes a footpedal module which enables the operator to control many parameters associated with the operation. Such parameters include the aspiration rate, the intensity power applied to phaco handpiece as well as modes of operation of the handpiece itself. Thus, the use of the handpiece is facilitated by delegating these control functions to the footpedal device.

Heretofore, footpedals have been limited to detecting angular foot movement, i.e. depression of the footpedal and lateral foot movement, i.e. side switches on the footpedal. In this arrangement a pedal plate is connected to an encoder to provide control for a specified function This, of course, limits the number of variables controllable by the footpedal.

Because of the importance of the control features provided by footpedals, such devices must be user friendly in order to provide a surgeon the comfort and reliability expected in order not to initiate any disruption of the surgeon's concentration when performing surgery.

For example additional switches are needed to effect "fast access" changes desired by a surgeon so that more direct control of the surgical apparatus can be performed by a surgeon's foot rather than by an assistant.

A computer for phacoemulsification may have three different settings. In each set, the flow rate, vacuum, and power level can be programmed. This is so called modern "Multiple Modulation Phacoemulsification" MMP capability. The switches of footpedal can be programmed as the trigger to initiate these MMP. Normally, MMP1 (or phacol is set for moderate aspiration rate, moderate vacuum level. MMP2, is set to more efficiently remove cracked nucleus, and MMP3 generates the least amount of flow turbulence which is most suitable for sculpting the nucleus.

Footpedal switch can be used to enter various modes of operation. For example, an "MMP UP" mode can enable a surgeon to scroll from MMP1 to MMP2 to MMP3. An "MMP Down" mode can enable a surgeon to scroll from MMP3 to MMP2 to MMP1. Alternately, an "MMP Rotate" switch mode can provide requested "Kicks" or "connects" in which the modes may rotate from MMP1-MMP2-MMP-3MMP1-MMPZ-etc.

As may be expected, different types of footpedals are preferred by various surgeons, with some surgeons preferring an accelerator type pedal in which the sole of the surgeon's foot is utilized for depression, while others desire a pedal operable by the surgeon's toe in order to depress the pedal.

In the past, this has led to the development of a multitude of footpedal devices of diverse configuration in order to provide the comfort and reliability desired by individual surgeons.

Unfortunately, when phacoemulsification apparatus is utilized by a number of physicians, a change in footpedals is often required, which is often inconvenient and may require recalibration of the apparatus. In addition, such alternative footpedals may not be available or offered by a manufacturer.

Accordingly, it is desirable to provide a footpedal which can be utilized by all attending physicians despite their preference for toe or sole activated pedals, while at the same time expanding the number of variables controllable by the footpedal. The present invention fulfills that need, while at the same time providing a footpedal which is comfortable to use in either a toe or sole depression configuration.

SUMMARY OF THE INVENTION

Apparatus in accordance with the present invention for controlling a handpiece during surgery generally includes a foot pedal which is pivotally mounted to a base for enabling depression thereof in order to provide control signals for handpiece operation. At least one support surface is disposed adjacent to the foot pedal on the base at a position enabling access thereto by a user's foot and a first ribbon switch is disposed on the support surface. The first ribbon switch has a length sufficient to enable actuation thereof by the user's foot without visual observation thereof by user. Importantly, the ribbon switch is actuable by depression thereof any point along the length of the switch. This feature facilities the use by a user without the visual observation of the switch.

A second support surface may be disposed adjacent to the foot pedal on the base at a position enabling access thereto by the user's foot. A second ribbon switch is disposed on the second support surface and has a length sufficient to enable acuation thereof by the user's foot without visual observation thereof by the user as similar to the first ribbon switch.

The surfaces may either be shrouds or fences disposed on either side of the foot pedal for enabling the ribbon switches to be disposed parallel to the foot pedal. The first and second ribbon switches enable the user to control at least two additional variables for controlling the handpiece.

In addition, a member may be provided which extends over the foot pedal in a generally transverse relationship therewith along with a third ribbon switch disposed on the member and having a length for enabling access thereto by a user's foot without visual observation thereof by the user.

Still another embodiment of the present invention utilizes a forth ribbon switch disposed in and end-to-end relationship with the third ribbon switch on the member. Because of the transverse position of the member and third and forth ribbon switches over the foot pedal, a right and left hand orientation is provided for the user when the end-to-end relationship of the third and forth ribbon switches is centered approximately over the foot pedal.

When the foot pedal is positioned on the base to enable depression by a user toe or sole, the first and second ribbon switches are of sufficient length to enable access thereto by either the user's toe or sole.

The present invention is also directed to an improvement to an existing foot pedal. In this embodiment, support surfaces are provided adjacent the existing foot pedal on a base at a position enabling access thereto by a user's foot along with the first and second ribbon switches as hereinabove described.

In addition, a member extending over the existing foot pedal may be provided along with third and forth ribbon switches to enable the user to control additional variables to a surgical handpiece, otherwise not possible with the original foot pedal.

BRIEF DESCRIPTION OF THE DRAWINGS

The advantages and features of the present invention will be. better understood by the following description when considered in conjunction with the accompanying drawing, in which:

FIG. 1 is a perspective view of apparatus for controlling handpiece during surgery in accordance with the present invention generally showing a foot pedal disposed between support surfaces along with ribbon switches disposed thereon for actuation for a user's foot along with the member spanning the foot pedal in a transverse manner which also includes one or more ribbon switches as will be hereinafter discussed in greater detail.

DETAILED DESCRIPTION

With reference to FIG. 1 there is shown apparatus 10 for controlling a handpiece (not shown) during surgery which includes a foot pedal 12 pivotally mounted to a base 14 for enabling a depression thereof in order to provide control signals for handpiece (not shown) operation. A foot pedal 12 may be similar or identical to known foot pedals such as, for example set forth in U.S. Pat. No. 5,983,749, issued Nov. 16, 1999 for Duel Position Foot Pedal for Ophthalmic Surgery apparatus or U.S. patent application Ser. No. 09/140,874 filed Aug. 29, 1998 for Back Flip Medical Foot Pedal.

The referenced patent and application are to be incorporated herewith in their entirety in order to describe the construction and operation of foot pedals suitable for incorporation into the present invention or which may be adapted with the features of the present invention in order to provide additional switches for controlling various surgical handpiece variables. In light of this incorporation, further discussion of the foot pedal 12 in its operation will not be made. As set forth in U.S. patent application Ser. No. 09/140,874, the foot pedal 12 may be positioned on the base 14 to enable depression by a user's toe or sole (not shown).

Support surfaces in the form of shrouds 20, 22 may be provided and disposed adjacently foot pedal 12 on opposite sides 23, 30 at a position enabling access thereto by a user's foot (not shown). The first and second foot activated ribbons switches 34, 36 to are disposed on the surfaces 20, 22 in a conventional manner such as gluing or the like, and have a length extending along the surfaces 20, 22 which is sufficient to enable actuation of the ribbon switches 34, 36 by a user's foot (not shown) without visual operation thereof by the user (not shown).

Ribbon switches 34, 36 suitable for the present invention, are available from Tapeswitch Corporation, ControlFlex Ribbon Switch 141-BH series from Farmingdale N.Y. 11735.

It is important that the ribbon switches 34, 36 have sufficient length as well as width, which can be activated. This is particularly important in the phacoemulsification procedures in which the surgeon's eye is concentrated on the patient. Beads 40, 42 may be incorporated into the ribbon switches 34, 36 in order to provide tactile alert of contact for the user. Preferably the shroud surfaces 20, 22 are relatively smooth with the exception of the ribbon switch and bead thereon which gives the surgeon an alert of foot contact therewith.

The shroud 20, 22 are curved to more or less align with the general slope of the foot pedal and accordingly the ribbon switches 34, 36 are bent and bonded thereto to provide a friendly angle of foot activation without jeopardizing the switch sensitivity.

The ribbon switch 34, 36 length enables the user to activate the switch whether the foot pedal 12 is utilized in a toe contact or a sole contact with the user's foot, this arrangement being more particularly set forth in the incorporated patent application Ser. No. 09/140,874.

Other support surfaces may be utilized as for example fence 50, 52 disposed along both sides 26, 30 of the foot pedal 12 which can support ribbon switches 54, 56, the switches 54, 56 being identical in function to the switches 34, 36 as hereinabove described but having a different length.

Additional ribbon switches 60, 62 may be disposed on a member 64 extending over the foot pedal in a transverse relationship. Preferably the switches 60, 62 are disposed in an end 66 to end 68 relationship with this end 66 to end 68 relationship being centered over the foot pedal. In this manner, a right and left hand relationship is established for the switches 60, 62 over the foot pedal 12. The switches 60 to 62 are similar or identical to the switches 34, 36, 50, 52 as hereinabove described.

Although there has been hereinabove described apparatus having a foot pedal, and improvements in existing foot pedals for controlling a hand piece during surgery for the purpose of illustrating the manner in which the invention may be used to advantage, it will be appreciated that the invention is not limited thereto. Accordingly, any and all modifications, variations, or equivalent arrangement which may occur to those skilled in the art, should be considered to be within the scope of the invention as defined in the appended claims.

What is claimed is:

1. Apparatus for controlling a handpiece during surgery, said apparatus comprising:

a foot pedal pivotally mounted to a base for enabling depression thereof in order to provide control signals for handpiece operation;

at least one support surface disposed adjacent to said foot pedal on said base at a position enabling access thereto by a user's foot; and a first ribbon switch disposed on said support surface and having a length sufficient to enable actuation thereof by the user's foot without visual observation thereof by the user, said ribbon switch being actuable by depression thereof at any point along a length of said first ribbon switch.

2. The apparatus according to claim 1 further comprises a second support surface disposed adjacent said foot pedal on said base at a position enabling access thereto by the user's foot and a second ribbon switch, disposed on said second support surface, having a length sufficient to enable actuation thereof by the user's foot without visual observation thereof by the user, said second ribbon switch being actuable by depression thereof at any point along a length of said second ribbon switch.

3. The apparatus according to claim 2 wherein the first and second support surfaces compose shrouds disposed as opposite sides of said foot pedal.

4. The apparatus according to claim 2 wherein the first and second support surfaces compose fences disposed on opposite sides of said foot pedal.

5. The apparatus according to claim 2 wherein the ribbon switches are disposed parallel to said foot pedal.

6. The apparatus according to claim 5 further comprising a member, extending over said foot pedal in a transverse relationship and a third ribbon switch disposed on said member at a position enabling actuation thereof by the user's foot without usual observation thereof by the user, said third ribbon switch being actuable by depression thereof at any point along a length of said third ribbon switch.

7. The apparatus according to claim 6 further comprising a fourth ribbon switch disposed on said member in an end-to-end relationship with said third ribbon switch, said end-to-end relationship being disposed over said foot pedal.

8. The apparatus according to claim 6 wherein said third ribbon switch has a length at least equal to a width of said foot pedal.

9. The apparatus according to claim 7 wherein a combined length of the third and for the ribbon switches is at least equal to a width of said foot pedal.

10. The apparatus according to claim 8 wherein said foot pedal is positioned on said base to enable depression by a user's toe or sole and the first and second ribbon switch are of sufficient length to enable access thereto by either of the user's toe or sole.

11. In apparatus having a footpedal for controlling a handpiece during surgery, an improvement comprising:

at least one shroud disposed adjacent said foot pedal at a position enabling access thereto by a user's foot; and a first ribbon switch disposed on said support surface and having a length sufficient to enable actuation thereof by the user's foot without visual observation thereof by the user, said ribbon switch being actuable by depression thereof at any point along a length of said first ribbon switch.

12. The improvement according to claim 11 further comprises a second support surface disposed adjacent said foot pedal at a position enabling access thereto by the user's foot on a second ribbon switch, disposed on said second support surface, having a length sufficient to enable actuation thereof by the user's foot without visual observation thereof by the user, said second ribbon switch being actuable by depression thereof at any point along a length of said second ribbon switch.

13. The improvement according to claim 12 wherein the first and second support surfaces compose shrouds disposed on opposite sides of said foot pedal.

14. The improvement according to claim 12 wherein the first and second support surfaces compose fences disposed on opposite sides of said foot pedal.

15. The improvement according to claim 12 wherein the ribbon switches are disposed parallel to said foot pedal.

16. The improvement according to claim 15 further comprising a member, extending over said foot pedal in a transverse relationship and a third ribbon switch disposed on said member at a position enabling actuation thereof by the user's foot without usual observation thereof by the user, said third ribbon switch being actuable by depression thereof at any point along a length of said third ribbon switch.

17. The improvement according to claim 16 further comprising a fourth ribbon switch disposed on said member in an end-to-end relationship with said third ribbon switch, said end-to-end relationship being disposed over said foot pedal.

18. The improvement according to claim 16 wherein said third ribbon switch has a length at least equal to a width of said foot pedal.

19. The improvement according to claim 17 wherein a combined length of the third and fourth ribbon switches is at least equal to a width of said foot pedal.

20. The improvement according to claim 15 wherein said foot pedal is configured for depression by a user's toe or sole and the first and second ribbon switch are of sufficient length to enable access thereto by either of the user's toe or sole.

* * * * *